(12) United States Patent
Hloucha et al.

(10) Patent No.: US 9,102,907 B2
(45) Date of Patent: Aug. 11, 2015

(54) USE OF CLEANING AGENTS CONTAINING MICROEMULSIONS THAT CONTAIN WAX

(75) Inventors: Matthias Hloucha, Köln (DE); Esther Küsters, Düsseldorf (DE); Jasmin Menzer, Monheim (DE); Daniela Prinz, Dormagen (DE); Martina Holz, Hilden (DE); Thomas Albers, Düsseldorf (DE); Werner Seipel, Hilden (DE); Jessica Erasmy, Köln (DE); Hermann Hensen, Haan (DE); Guadalupe Pellón, Düsseldorf (DE); Sybille Cornelsen, Ratingen (DE); Norbert Boyxen, Kempen (DE)

(73) Assignee: Cognis IP Management GmbH, Duesseldorf (DE)

( * ) Notice: Subject to any disclaimer, the term of this patent is extended or adjusted under 35 U.S.C. 154(b) by 257 days.

(21) Appl. No.: 13/636,271

(22) PCT Filed: Mar. 9, 2011

(86) PCT No.: PCT/EP2011/001136
§ 371 (c)(1),
(2), (4) Date: Sep. 20, 2012

(87) PCT Pub. No.: WO2011/116881
PCT Pub. Date: Sep. 29, 2011

(65) Prior Publication Data
US 2013/0012423 A1 Jan. 10, 2013

(30) Foreign Application Priority Data
Mar. 23, 2010 (EP) .................................... 10003051

(51) Int. Cl.
| | | |
|---|---|---|
| *C11D 1/66* | (2006.01) | |
| *C11D 3/22* | (2006.01) | |
| *C11D 3/43* | (2006.01) | |
| *C11D 17/00* | (2006.01) | |
| *C11D 1/825* | (2006.01) | |

(52) U.S. Cl.
CPC ............ *C11D 17/0021* (2013.01); *C11D 1/825* (2013.01); *C11D 1/662* (2013.01); *C11D 1/667* (2013.01)

(58) Field of Classification Search
CPC .............. C11D 1/66; C11D 3/22; C11D 3/43; C11D 7/5004; C11D 17/0017; C11D 17/0021
See application file for complete search history.

(56) References Cited

U.S. PATENT DOCUMENTS

| | | |
|---|---|---|
| 6,303,109 B1 | 10/2001 | Foerster et al. |
| 6,468,551 B1 | 10/2002 | Diec et al. |
| 6,821,939 B1 | 11/2004 | Szewczyk et al. |
| 8,343,470 B2 | 1/2013 | Hloucha et al. |
| 8,715,631 B2 * | 5/2014 | Araujo et al. ............... 424/70.13 |
| 2002/0010114 A1 | 1/2002 | Dufay et al. |
| 2003/0118534 A1 * | 6/2003 | Bruning et al. .................. 424/66 |
| 2006/0122246 A1 * | 6/2006 | Msika et al. ................... 514/374 |
| 2006/0204468 A1 * | 9/2006 | Allef et al. .................. 424/70.13 |
| 2007/0160651 A1 * | 7/2007 | Mueller et al. ................ 424/443 |
| 2007/0160652 A1 * | 7/2007 | Mueller et al. ................ 424/443 |
| 2007/0265209 A1 * | 11/2007 | Goget et al. ...................... 514/23 |
| 2009/0131542 A1 * | 5/2009 | Issberner et al. .............. 514/777 |
| 2009/0196837 A1 * | 8/2009 | Msika et al. ...................... 424/59 |
| 2010/0311627 A1 | 12/2010 | Hloucha et al. |
| 2011/0287073 A1 | 11/2011 | Strauss et al. |
| 2012/0039823 A1 * | 2/2012 | Kolbe et al. ...................... 424/59 |
| 2012/0094919 A1 * | 4/2012 | Graub et al. .................. 514/18.8 |
| 2013/0149272 A1 * | 6/2013 | Hloucha et al. ............. 424/70.13 |

FOREIGN PATENT DOCUMENTS

| | | |
|---|---|---|
| CA | 1086652 | 9/1980 |
| DE | 3534733 | 4/1987 |
| EP | 0559304 | 6/1990 |
| EP | 0410567 | 1/1991 |
| EP | 0813861 | 12/1997 |
| EP | 1152051 | 11/2001 |
| EP | 1767554 | 3/2007 |
| EP | 2368972 | 9/2011 |
| FR | 2252840 | 6/1975 |
| WO | WO-98/15255 | 4/1998 |
| WO | WO-98/40044 | 9/1998 |
| WO | WO-9948473 | 9/1999 |
| WO | WO-00/71658 | 11/2000 |
| WO | WO-2008/019773 | 2/2008 |
| WO | WO 2008/155073 | 12/2008 |
| WO | WO-2008/155075 | 12/2008 |

* cited by examiner

*Primary Examiner* — Charles Boyer
(74) *Attorney, Agent, or Firm* — Servilla Whitney LLC

(57) ABSTRACT

The invention relates to the use of microemulsions, containing (a) at least one alkyl(oligo)glycoside, (b) at least one co-surfactant different from (a), (c) at least one water-insoluble organic oil component, (d) at least one wax, and (e) water, to produce cleaning agents, and aqueous hand dishwashing detergents, containing anionic and amphoteric surfactants and, in amounts from 0.2 to 10 wt % relative to the total weight of the hand dishwashing detergents, a microemulsion according to the description in claim 1, and cosmetic cleaning agents, containing A) a microemulsion according to the description in claim 1, B) anionic surfactants, C) cationic polymers, D) optionally additional surfactants, E) optionally cosmetic additives, and F) water.

17 Claims, No Drawings

USE OF CLEANING AGENTS CONTAINING MICROEMULSIONS THAT CONTAIN WAX

The invention is in the field of cleaning agents firstly for use as skin-friendly hand dishwashing detergents and secondly for use as cosmetic cleaning agents which are present in the form of finely divided emulsions based on oil-containing microemulsions which contain waxes and further relates to the use in hand dishwashing detergents or in cosmetic cleaning agents such as shower gels.

Cleaning agents are generally emulsions of greater or lesser concentration which, as is known, comprise in particular surfactants and care substances besides oil components. On the part of the consumer, there is the desire for those preparations which are not only particularly skin-friendly, but remove especially oily soilings—in the widest sense also decorative cosmetics—rapidly and residue-free. In many cases, the manufacturer of such end preparations will refrain from mixing the individual feed materials itself; it will instead attempt to fall back on so-called "all-purpose compounds". These are understood as meaning mixtures which can serve as the basis for the very wide variety of end products. These mixtures are being increasingly supplied as microemulsions with diverse advantages. In the simplest case, the concentrated microemulsions are diluted to the application concentration by adding water, in which case they themselves constitute the agents. However, as a rule, corresponding additives will be added to them. Depending on the field of use of these "all-purpose compounds" in the form of a microemulsion, different requirements are set which, in the best case are already satisfied by the microemulsion. In individual cases, further components have to be added which satisfy these requirements without destroying the positive features of the microemulsion.

In the area of application of non-cosmetic cleaning agents such as, for example, for the manual cleaning of dirty dishes, concentrated aqueous surfactant solutions are usually used, on which a whole series of sometimes very different requirements are nowadays placed. The agents should
- have the highest possible content of active substance,
- at the same time be liquid or at least flowable
- have the lowest possible low-temperature cloud point,
- develop a strong, resistant foam even if the liquor has a high fat content, and simultaneously naturally
- have a high plate-washing capacity,
- be dermatologically acceptable, i.e. non-skin-irritating, even in concentrated form.

The point relating to dermatological acceptability deserves particular attention since consumer expectations have risen in recent years in this respect. Against the background of an increasing number of consumers who have sensitive skin, agents which have advantageous properties in this regard are becoming more and more important.

WO 00/71658 proposes incorporating a skin-friendly polymeric agent as foam stabilizer into hand dishwashing detergents in order, in this way, to produce cleaning agents that do not irritate skin.

EP 0 410 567 A1 proposes making hand dishwashing detergents more skin-friendly by adding certain skin-friendly additives selected from the group of hydrocarbons, esters, amines, amides, quaternary ammonium compounds or alcohols. One selected component is waxes, in particular beeswax. The agents according to the teaching of the specification are produced by melting the solid ingredients and then stirring with the aqueous phase at temperatures of >70° C.

Although there is a large number of skin-friendly hand dishwashing detergents on the market nowadays, there is nevertheless an intense interest, both by the raw material suppliers and the manufacturers, to find agents which better satisfy the required objective than the products of the prior art. This applies in particular with regard to the simplest possible production method for such agents.

In the field of cosmetic cleaning agents, there is likewise a need to find agents which better satisfy the expectations of the end consumers as well as those of the end product manufacturers.

After washing, skin and hair often feel rough and brittle, particularly if they have already been damaged by environmental influences. Moreover, hair can also be damaged by coloring or perming and is often characterized by a dry, straw-like feel after hair washing.

It is therefore the aim of the cosmetic cleaning agents to compensate for the loss of sebum and water in skin and hair that is caused by daily washing. The bodycare products should protect against environmental influences, in particular against sun and wind, and delay skin ageing.

For this reason, conditioners are often used in shampoo compositions which are intended to counteract these disadvantages. Shampoo compositions are therefore often found which comprise silicones as conditioners. However, these can attach irreversibly to the hair and, in so doing, for their part cause negative effects on the feel, and in the worst case even to problems during the coloring and perming of hair.

In many cosmetic preparations, oils and waxes are suitable as conditioning agents. However, these are nowhere near as marked in their effect as silicones. These oils and waxes can hitherto only be stabilized in the preparations in small amounts.

WO2008155075 describes cosmetic preparations which comprise a microemulsion and at least one cationic polymer as well as non-alkoxylated surfactants. These preparations are used as conditioning agents in shampoo and hair treatment agents. The microemulsion comprises APG, glycerol monoester, an oil body and water. To achieve a better conditioning effect, a cationic polymer must obligatorily be used.

A disadvantage of the microemulsions of the prior art is the fact that, besides the three main constituents surfactant, cosurfactant and oil phase, the incorporation of highly viscous, wax-like substances is very difficult.

When providing microemulsions with anionic, cationic or amphoteric surfactants, it is also problematic that the oil components can be used only with very great difficulty since the surfactants are often too water-soluble and therefore scarcely have emulsifying properties.

DE 3534733 describes microemulsions, although the fraction of the solubilized oil components in the range from 0.5 to 3% by weight is low. The problem of incorporating larger amounts of oil also becomes apparent in WO 9948473; here, the incorporation of just 0.5-1% by weight of oil is discussed.

It is known that oil-in-water emulsions which are produced with non-ionic emulsifiers often suffer from phase inversion upon heating, i.e. at elevated temperatures, the external, aqueous phase can become the internal phase. This process is generally reversible, meaning that, upon cooling, the original emulsion type is reformed again. Emulsions which have been produced above the phase inversion temperature generally have a low viscosity and high storage stability.

For example, WO 98/40044 describes aqueous preparations of water-soluble surfactants which have lipid-surfactant mixed micelles with an average particle size of below 500 nm and thus appear bluish-white. The subject matter of WO 98/15255 is microemulsion gels of the oil-in-water type in which the oil droplets are stabilized in the water phase by associative thickeners.

The object of the present invention was therefore to provide skin-friendly cleaning agents and specifically hand dishwashing detergents and cosmetic cleaning agents which better satisfy the required objects than known products, the cleaning behavior of which corresponds to the prior art, or, in the best case, even surpasses this, and which leave behind a pleasant skin feel following application to the skin. On the skin, a feeling of a soft, richly cared-for skin should arise, and any cleaned hair should be given a pleasant feel without a greasy feel being left behind.

It is a further object of the present invention to provide oil-containing cleaning products which can be applied to the skin in a sensorily pleasant manner, spread and washed off, with the skin-care oil phase remaining on the skin. Furthermore, the agents should leave behind a long-lasting care and pleasant skin feel without losing the cleaning effect during the rinsing operation.

The cleaning agent should comprise microemulsions which can be readily formulated, are stable over a prolonged period and already include the property of conveying a pleasant skin feel.

Moreover, the aim was to provide cosmetic hair care agents, the conditioning performance of which corresponds to that of silicone-containing preparations or, in the best case, even surpasses this.

It has now been found that certain emulsions are able to achieve the object set above.

It could not have been foreseen by the person skilled in the art that the object could be achieved through the use of a microemulsion and/or by a finely divided emulsion which comprises this microemulsion which is characterized by the mixing of surfactant, cosurfactant, and a mixture of organic phase and waxes.

Thanks to the microemulsion, this cleaning agent component is present in the form of a low viscosity agent and can be incorporated very readily into any type of cleaning and care agent, such that transparent or slightly cloudy products can be produced. Preference is given to the use as non-cosmetic cleaning agent in hand dishwashing detergents or as cosmetic cleaning agent in shower gel formulations or shampoo preparations. Consequently, the preferred use in combination formulations for skin and hair (two in one products) is also obvious. It was possible to show that a microemulsion comprising a wax component and, as oil phase, at least one ester oil exhibits excellent properties as cosmetic cleaning agent in bodycare because the combination of these two oil components leads to the fact that a pleasant long-lasting care skin feel can be felt. The two oil bodies lead in their combination to a long-lasting adhesion to skin and hair without being greasy and/or leaving behind an unpleasant greasy feel since they are present in the microemulsion in incorporated form. This effect was able to be demonstrated by means of deposition tests. For a shower gel formulation, it is also highly advantageous that a wax-containing microemulsion based on ester oils in combination with cationic polymers significantly improves the skin feel after the showering process. This was demonstrated in sensory tests.

A further advantage of the microemulsion to be used according to the invention is that it is preferably free of alkoxylated compounds and can thus also be incorporated into cosmetic products for which the consumer attaches increased importance to "green cosmetics".

A first subject matter of the present application is directed to the use of microemulsions comprising
   (a) at least one alkyl(oligo)glycoside,
   (b) at least one cosurfactant different from (a),
   (c) at least one non-water-soluble organic oil component,
   (d) at least one wax and
   (e) water
for producing cleaning agents.

Furthermore, the microemulsions can comprise a cationic compound, in particular quaternary ammonium compounds, or a cationic polymer as additional component (f). Quaternary ammonium compounds are understood here as meaning in particular quaternized fatty acid triethanolamine ester salts. However, alkylammonium halides are likewise suitable.

Furthermore, optionally further ingredients are also possible, such as biocides, preservatives, pH regulators, dyes, antifoams, or perfumes as component (g). When used for producing hand dishwashing detergents, pH regulators, in particular inorganic or organic acids, such as citric acid or benzoic acid, and also biocides and/or preservatives are preferably present here. When used for producing cosmetic cleaning agents, preference is given to cosmetic additives, which are described in more detail later in the text.

The microemulsion used according to the invention can be used in the form of or as dilute solution. For use in cosmetic cleaning agents such as shampoo, baby care products, foam bath, bath oil, the microemulsion can be used directly or be formulated with customary additives such as foam formers, thickeners, cationic polymers, preservatives, active ingredients. For the use as shower gel, the addition of foam formers and thickeners is preferred in order to obtain a gel-like consistency. For the use as impregnating agent for sheet-like structures, a dilution with water is preferred.

In a preferred embodiment, the microemulsion is used, comprising:
   (a) 1-35% by weight of at least one alkyl(oligo)glycoside
   (b) 1-30% by weight of at least one cosurfactant
   (c) 5-60% by weight of an organic oil phase
   (d) 0.5-15% by weight of at least one wax component
   (e) water ad 100% by weight
   (f) 0-10% by weight of cationic polymers
   (g) 0-10% by weight of further ingredients.

In a further preferred embodiment, a microemulsion is used for producing hand dishwashing detergents comprising (all data based on active substance (AS)):
   4-25% by weight of component (a)
   4-20% by weight of component (b)
   5-50% by weight of component (c)
   0.5-15% by weight of component (d)
   10-65% by weight of component (e)
   0-10% by weight of component (f)
   0-5% by weight of further ingredients (g),
with the proviso that the sum of (a) to (g) gives 100.

In a particularly preferred embodiment, a microemulsion is used for producing cosmetic cleaning agents comprising:
   (a) 10-25% by weight of at least one alkyl(oligo)glycoside
   (b) 10-20% by weight of at least one cosurfactant
   (c) 10-50% by weight of an organic oil phase comprising ester oils
   (d) 0.5-10% by weight of at least one wax component
   (e) water ad 100% by weight
   (g) 0-10% by weight of cosmetic additives.

The microemulsion which is used for producing cosmetic cleaning agents consists particularly preferably of a) to g) in the quantitative ratios specified in the paragraph above.

According to the invention, the particles are present in finely divided form in the microemulsion or in the cosmetic cleaning and care agents. Within the context of the invention, "finely divided" means an average particle size, specifically 3 to 100 nm for the particles in the microemulsion, and upon dilution of the microemulsion a particle size≤5000 nm. The particle size is determined in accordance with the DLS method using an instrument called Horiba LB-500.

Microemulsion

Microemulsions are known per se. Microemulsions are macroscopically homogeneous, optically transparent, low viscosity, thermodynamically stable mixtures. Depending on the type of surfactant used, the microemulsion exhibits a temperature-dependent phase behavior. Particularly some non-ionic surfactants, and here in particular surfactants whose hydrophilic molecular moieties are formed from ethoxy or propoxy groups, lead to a characteristic temperature-dependent phase behavior in microemulsions.

A prerequisite of the formation of microemulsions is an extremely low interfacial tension between the water-rich phase and the oil-rich phase. For the microemulsions, this can assume values between $10^{-1}$ and $10^{-5}$ mNm$^{-1}$.

The average particle sizes of the microemulsions are usually below 100 nm, preferably between 3 and 100 nm. They have a high transparency and are stable against visible phase separation upon centrifugation at 2000 rpm for at least 30 minutes. The microemulsions within the context of the present teaching preferably exhibit an average particle size of less than 100 nm. The conductivity of the microemulsions according to the invention is preferably in the range greater than/equal to 500 µSi/cm and particularly preferably greater than/equal to 1000 µSi/cm. A preferred range is 800 to 1500 µSi/cm. The microemulsions according to the invention are preferably transparent, in particular they exhibit a transparency greater than/equal to 80% at 40° C., with transparency values greater than 90% at 40° C. being typical. Preference is given to those microemulsions which have a transparency, measured at 40° C., of 95 to 100%.

The microemulsions are preferably produced simply by mixing the oil phase with the other oil-soluble ingredients, heating the oil phase to above the melting point of all of the constituents and subsequently adding the aqueous surfactant-containing phase. Alternatively, the heated oil phase can also be added to the aqueous phase. The thermodynamically stable microemulsion is then formed spontaneously, additionally with stirring if necessary.

The microemulsions according to the present teaching are preferably of the oil-in-water (O/W) type or have a bicontinuous structure. The microemulsions comprise, as the outer phase, thus preferably water, and also alkyl (oligo)glycosides and a cosurfactant different therefrom, and also an oil component and a wax. However, the microemulsions can also be present as water-in-oil emulsion.

Component (a)

As component (a) of the present invention, preference is given to using microemulsions based on alkyl(oligo)glycosides.

Alkyl and alkenyl oligoglycosides are known nonionic surfactants which conform to the general formula (I),

$$R^1O\text{-}[G]_p \qquad (I)$$

in which $R^1$ is an alkyl and/or alkenyl radical having 4 to 22 carbon atoms, G is a sugar radical having 5 or 6 carbon atoms and p is numbers from 1 to 10. They can be obtained by the relevant methods of preparative organic chemistry. The alkyl and/or alkenyl oligoglycosides can be derived from aldoses or ketoses having 5 or 6 carbon atoms, preferably glucose. The preferred alkyl and/or alkenyl oligoglycosides are therefore alkyl and/or alkenyl oligoglucosides. The index number p in the general formula (I) indicates the degree of oligomerization (DP), i.e. the distribution of mono- and oligoglycosides, and is a number between 1 and 10. Whereas p in any given compound must always be a whole number and here in particular can assume the values p=1 to 6, the value p for a specific alkyl oligoglycoside is an analytically determined calculated parameter which, in most cases, is a fractional number. Preference is given to using alkyl and/or alkenyl oligoglycosides with an average degree of oligomerization p of from 1.1 to 3.0. From the point of view of application, preference is given to those alkyl and alkenyl oligoglycosides whose degree of oligomerization is less than 1.7 and in particular is between 1.2 and 1.4. The alkyl or alkenyl radical $R^1$ can be derived from primary alcohols having 4 to 11, preferably 8 to 10, carbon atoms. Typical examples are butanol, caproic alcohol, caprylic alcohol, capric alcohol and undecyl alcohol, and also technical-grade mixtures thereof, as are obtained for example during the hydrogenation of technical-grade fatty acid methyl esters or in the course of the hydrogenation of aldehydes from the Roelen oxo synthesis. Preference is given to alkyl oligoglucosides of chain length $C_8$-$C_{10}$ (DP=1 to 3) which are produced as forerunning in the distilled separation of technical-grade $C_8$-$C_{18}$ coconut fatty alcohol and can be contaminated with a fraction of less than 6% by weight of $C_{12}$-alcohol, and also alcohol oligoglucosides based on technical-grade $C_{9/11}$ oxo alcohols (DP=1 to 3). The alkyl or alkenyl radical $R^1$ can also be derived from primary alcohols having 12 to 22, preferably 12 to 14, carbon atoms. Typical examples are lauryl alcohol, myristyl alcohol, cetyl alcohol, palmoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol, and also technical-grade mixtures thereof which can be obtained as described above. Preference is given to alkyl oligoglucosides based on hydrogenated $C_{12/14}$ coconut alcohol with a DP of from 1 to 3.

The microemulsions within the context of the present teaching comprise the component (a) preferably in amounts of from 1 to 35% by weight, based on the total weight of the microemulsion and for the use for producing hand dishwashing detergents preferably in amounts of from 2 to 30% by weight and in particular 4 to 25% by weight. For the use for producing cosmetic cleaning agents, amounts of from 10 to 30% by weight, particularly preferably from 15 to 25% by weight, based on the total weight of the microemulsion, are present.

Component (b) Cosurfactant

As a further obligatory component, the microemulsions comprise at least one cosurfactant which must be structurally different from the component (a) and is a polyol fatty acid ester. Within the context of the invention, polyols whose fatty acid esters are used as cosurfactants include alcohols with at least three carbon atoms and at least three hydroxyl groups.

Of suitability for producing hand dishwashing detergents are also in particular nonionic surfactants, such as fatty alcohol alkoxylates and derivative thereof.

A particularly preferred group of cosurfactants within the context of the present teaching for the production of hand dishwashing detergents, however, is the esters of glycerol. Very particular preference is given to monoesters of glycerol, where fatty acid having 12 to 22 carbon atoms are particularly preferred as acid component. In particular, monocarboxylic acids which can either be linear or branched, are suitable. Particular preference is given to linear fatty acids which contain at least one C—C double bond, where oleic acid is to be mentioned here as a preferred example. Consequently, a component (b) to be selected with advantage for the use of microemulsions for producing hand dishwashing detergents is glycerol monooleate. As a result of production, in standard commercial monoglycerides, minor amounts (e.g. less than 5 or less than 1% by weight) of di- and triglycerides, or free glycerol may also be presented without this impairing the effect of the monoglyceride. For producing hand dishwashing detergents, the cosurfactants are present preferably in amounts of from 1 to 20% by weight, based on the total weight of the microemulsion and in particular in amounts of from 4 to 20% by weight and 4 to 15% by weight.

For producing cosmetic cleaning agents, preferred cosurfactants are fatty acid esters of polyols which are selected from the group which is formed from sugar esters, W/O emulsifiers such as sorbitan esters, sorbitol partial esters, polysorbates, polyglyceryl esters, polyglyceryl partial esters, specifically, for example, polyglyceryl-2 dipolyhydroxystearate, polyglyceryl-3 diisostearate. Furthermore, preferred cosurfactants for producing cosmetic cleaning agents are mono- and dihydric alcohols of linear or branched alkanes.

For producing cosmetic cleaning agents, the cosurfactants are present preferably in amounts of 10-20% by weight, particularly preferably in amounts of 4-20% by weight, based on the total weight of the microemulsion.

The cosurfactants can also be used in the form of a mixture.

Component (c) Organic Oil Phase

The microemulsions within the context of the present teaching comprise, as further obligatory constituent, a water-insoluble so-called oil phase which comprises at least one oil component, i.e. a non-water-soluble organic phase. Preferably in amounts of from 5 to 60% by weight, based on the total weight of the microemulsion.

Preferably, the microemulsions comprise water-insoluble oil components or oil phases selected from the group of Guerbet alcohols based on fatty alcohols having 6 to 18 carbon atoms, esters of linear $C_6$-$C_{22}$ fatty acids with linear or branched $C_6$-$C_{22}$ fatty alcohols or esters of branched $C_6$-$C_{13}$ carboxylic acids with linear or branched $C_6$-$C_{22}$ fatty alcohols, esters of linear $C_6$-$C_{22}$ fatty acids with branched alcohols, esters of $C_6$-$C_{22}$ fatty alcohols and/or Guerbet alcohols with aromatic carboxylic acids, triglycerides based on $C_6$-$C_{10}$ fatty acids, esters of $C_2$-$C_{12}$ dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$ fatty alcohol carbonates, Guerbet carbonates based on fatty alcohols having 6 to 18, preferably 8 to 10, carbon atoms, esters of benzoic acid with linear and/or branched $C_6$-$C_{22}$-alcohols, linear or branched, symmetrical or asymmetrical dialkyl ethers having 6 to 22 carbon atoms per alkyl group, aliphatic or naphthenic hydrocarbons and dialkylcyclohexanes. For the use for producing hand dishwashing detergents, the water-insoluble oil components is used preferably in amounts of 5-50% by weight, based on the total weight of the microemulsion. For hand dishwashing detergents, preferred oil phases are also liquid mono-/di-/triglyceride mixtures based on $C_6$-$C_{18}$ fatty acids, where the di- and triglyceride content is greater than 5% by weight, ring-opening products of epoxidized fatty acid esters with polyols and/or silicone oils.

For the use for producing cosmetic cleaning agents, the water-insoluble oil components is used preferably in amounts of 5-50% by weight, preferably 10 to 50% by weight of active substance, based on the total weight of the microemulsion. For cosmetic cleaning agents, preferred organic oil phases, with the exception of alkoxylated compounds, are liquid ester oils, i.e. esters of linear $C_6$-$C_{22}$ fatty acids with linear or branched $C_6$-$C_{22}$ fatty alcohols or esters of branched $C_6$-$C_{13}$ carboxylic acids with linear or branched $C_6$-$C_{22}$ fatty alcohols, esters of linear $C_6$-$C_{22}$ fatty acids with branched alcohols, esters of $C_{18}$-$C_{38}$ alkyl hydroxycarboxylic acids with linear or branched $C_6$-$C_{22}$ fatty alcohols, esters of linear and/or branched fatty acids with polyhydric alcohols and/or Guerbet alcohols, esters of $C_6$-$C_{22}$ fatty alcohols and/or Guerbet alcohols with aromatic carboxylic acids, where the esters of fatty acids having more than 14 carbon atoms and alcohols having more than 14 carbon atoms are included among the waxes according to the invention if they are solid at 21° C. Furthermore, triglycerides based on $C_6$-$C_{10}$ fatty acids, esters of $C_2$-$C_{12}$ dicarboxylic acids with linear or branched alcohols having 1 to 22 carbon atoms or polyols having 2 to 10 carbon atoms and 2 to 6 hydroxyl groups, vegetable oils, linear and branched $C_6$-$C_{22}$ fatty alcohol carbonates.

Particular preference is given to the ester oils selected from the group which is formed from isopropyl palmitate, isopropyl myristate, ethyl hexyl palmitate, ethyl hexyl stearates, di-n-octyl carbonates, caprylyl caprylate, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate, dioctyl malate, propylene glycol, dimerdiol or trimertriol or mixtures thereof. Of these ester oils, particular preference is given to caprylyl caprylate, cococaprylate and dialkyl carbonates.

The organic oil phase for the case of cosmetic cleaning agents particularly preferably consists of liquid ester oils.

Besides the oils, fat-like substances such as lecithins and phospholipids are also suitable. The term lecithins is understood by the person skilled in the art as meaning those glycerophosolipids which are formed from fatty acids, glycerol, phosphoric acid and choline by esterification. Lecithins are therefore also often referred to as phosphatidylcholines (PC) in the expert world. Examples of natural lecithins which may be mentioned are the cephalins, which are also referred to as phosphatidic acids and are derivatives of 1,2-diacyl-sn-glyceryl-3-phosphoric acid. By contrast, phospholipids are usually understood as meaning mono- and preferably diesters of phosphoric acid with glycerol (glycerol phosphates), which are generally included among the fats. In addition, sphingosines and/or sphingolipids are also suitable. Tocopherols and essential oils are likewise suitable as oil component.

Hydrocarbons is the term used to refer to organic compounds which consist only of carbon and hydrogen. They include both cyclic and acyclic (=aliphatic) compounds. They include both saturated and mono- or polyunsaturated compounds. The hydrocarbons may be linear or branched. Depending on the number of carbon atoms in the hydrocarbon, the hydrocarbons can be divided into odd-numbered hydrocarbons (such as, for example, nonane, undecane, tridecane) or even-numbered hydrocarbons (such as, for example, octane, dodecane, tetradecane). Depending on the type of branching, the hydrocarbons can be divided into linear (=unbranched) or branched hydrocarbons. Saturated, aliphatic hydrocarbons are also referred to as paraffins.

Component (d)—Waxes

As further constituent, the microemulsions comprise waxes. These may also be present in a mixture with the oils specified in the previous paragraph. Within the context of the invention, waxes are natural substances of animal or vegetable origin which are solid at room temperature (21° C.) but generally have a certain shapeability. Waxes are insoluble in water but soluble in oils and capable of forming water-repellent films.

Typical examples of waxes within the context of the present teaching for the use for producing cleaning agents in general are natural waxes, such as e.g. shorea stenoptera butter (Cegesoft SH), shea butter, candelilla wax, carnauba wax, Japan wax, esparto grass wax, cork wax, guaruma wax, rice germ oil wax, sugar cane wax, ouricury wax, montan wax, beeswax, shellac wax, spermaceti, lanolin (wool wax), uropygial grease, ceresine, ozokerite (earth wax), petrolatum, paraffin waxes, micro waxes; chemically modified waxes (hard waxes), such as e.g. montan ester waxes, sasol waxes, hydrogenated jojoba waxes, and also synthetic waxes, such as e.g. polyalkylene waxes and polyethylene glycol waxes. Furthermore, esters of long-chain fatty acids (at least 14 carbon atoms) with long-chain fatty alcohols (at least 14 carbon atoms) such as myristyl myristate (Cetiol MM) or $C_{16}$-$C_{18}$ triglycerides of olus oil (Cegesoft PS6) fall under the term waxes.

For the use for producing hand dishwashing detergents, in particular esters of monocarboxylic acids having at least 14 carbon atoms with fatty alcohols having at least 14 carbon atoms are intended as waxes. For the use for producing cosmetic cleaning agents, the natural waxes are particularly preferred and, among these, shea butter is especially preferred. Shea butter (also shea fat, karité fat or carité fat, galam butter) is a natural solid fatty substance which is obtained from the plant *butyrospermum parkii*, the African shea butter tree, and is available in commercial amounts. Its melting range is 35 to 42° C. Usually, shea butter comprises 89 to 98% by weight of triglycerides, glycerol partial esters and free fatty acids, and also a content of 2 to 11% by weight of unsaponifiable fractions, of which hydrocarbons ("karitenes"), triterpene alcohols and sterols are the most important.

Component (e) Water

A further essential constituent of the microemulsions and of the cosmetic agent is water. The water should preferably be demineralized. The microemulsions preferably comprise up to 90% by weight of water.

For the use for producing hand dishwashing detergents, amounts of from 10 to 75% by weight and in particular from 15 to 65% by weight are preferred.

Preferred ranges for the water fraction in the microemulsion for the use for producing cosmetic cleaning agents are amounts of from 5 to 60, particularly from 5 to 50%, by weight and in particular from 10 to 40% by weight of water in the microemulsion. For the cosmetic cleaning agents, a preferred water fraction of greater than 80% by weight, based on the total amount of the cosmetic cleaning agents, arises. This means that the fraction of water from the microemulsion present is included in the 80% by weight. Likewise, water from the other ingredients, which are never free from water, is included.

Further Ingredients

In addition, the microemulsions can comprise, as additional component (f), a cationic compound, in particular quaternary ammonium compounds or a cationic polymer. Quaternary ammonium compounds are understood here as meaning in particular quaternized fatty acid triethanolamine ester salts. Likewise of suitability, however, are alkylammonium halides.

Suitable cationic polymers are, for example, cationic cellulose derivatives, such as e.g. a quaternized hydroethyl cellulose, cationic starch, copolymers of diallyl ammonium salts and acrylamides, quaternized vinylpyrrolidone/vinylimidazole polymers, such as e.g. Luviquat (BASF), condensation products of polyglycols and amines, quaternized collagen polypeptides, such as, for example, lauryldimonium hydroxypropyl hydrolyzed collagen (Lamequat), quaternized wheat polypeptides, polyethyleneimine, cationic silicone polymers, such as e.g. amidomethicones, copolymers of adipic acid and dimethylaminohydroxypropyldiethylenetriamine (Cartaretins), copolymers of acrylic acid with dimethyldiallylammonium chloride (Merquat 550), polyaminopolyamides, as described e.g. in FR-A 2252840, and also their crosslinked water-soluble polymers, cationic chitin derivatives, such as, for example, quaternized chitosan, optionally in microcrystalline distribution, condensation products of dihaloalkylene, such as e.g. dibromobutane with bisdialkylamines, such as e.g. bis-dimethylamino-1,3-propane, cationic guar gum, quaternized ammonium salt polymers, such as, e.g. Mirapol A-15, Mirapol AD-1, Mirapol AZ-1 from Miranol.

Further preferred cationic polymers are selected from the group of homopolymers or copolymers of ester or amide derivatives of acrylic acid or methacrylic acid (e.g. INCI: Polyquaternium-7, or PQ-7), homopolymers of methacryloylethyltrimethylammonium chloride (INCI: Polyquaternium-37, or PQ-37), quaternary copolymers of hydroxyethyl cellulose and diallyldimethylammonium chloride (INCI: Polyquaternium-4, or PQ-4), polymeric quaternized ammonium salts of hydroxyethylcellulose modified with a trimethylammonium-substituted epoxide (INCI: Polyquaternium-10, or PQ-10), depolymerized guar gum derivatives which are quaternized (INCI: Guar Hydroxypropyl Trimonium Chloride) or quaternized guar derivatives and quaternary copolymers of hydroxyethylcellulose and diallyldimethylammonium chloride. In a preferred embodiment, the cationic polymer is selected from the group which is formed from Polyquaternium-7, Polyquaternium-10 and cationic guar derivatives.

Furthermore, cationic polymers according to the teaching of EP 1 767 554 A1 can advantageously be used, which are sold by the applicant under the name Polyquart Pro. The microemulsions according to the invention preferably comprise 0.05 to 2% by weight of these cationic polymers.

The cosmetic cleaning agents according to the invention comprise the specified cationic polymers as component C). Here too, the preferred cationic polymers are selected from the group which is formed from Polyquaternium-7, Polyquaternium-10 and cationic guar derivatives. In a particularly preferred embodiment, preference is given to cationic guar derivatives since these are in keeping with the "green" concept.

Component (g)—Further Ingredients

Furthermore, possible optional further ingredients for the microemulsion are those selected from the group formed from hydrotopes such as glycerol, preservatives, citric acid, phenoxyethanol, UV photoprotective filters, antioxidants, biogenic active ingredients, perfume, dyes, biocides, antifoams, and pH regulators.

Preferably, for the use for producing hand dishwashing detergents, pH regulators, in particular inorganic or organic acids, such as citric acid or benzoic acid, and also biocides and/or preservatives are present.

These optional components are present in the microemulsions in total preferably in amounts of from 1 to 30% by weight and in particular in amounts of from 2 to 15% by weight, in each case based on the total weight of the microemulsion.

The specified further ingredients for the microemulsion used according to the invention can, within the context of the invention, also be present as component E) in cosmetic cleaning agents.

Besides the specified further ingredients, the microemulsion and/or the cosmetic cleaning agents which comprise the microemulsion can also comprise further customary cosmetic auxiliaries and additives which are known to the person skilled in the art, such as, for example, mild surfactants, emulsifiers, pearlescent waxes, stabilizers, salt, thickeners, consistency regulators, self-tanning agents, pigments, antioxidants, antidandruff agents, film formers, swelling agents, insect repellents, deodorant and antiperspirant active ingredients, biogenic active ingredients. Preferred biogenic active ingredients here are in particular tocopherol, tocopherol acetate, tocopherol palmitate, deoxyribonucleic acid, coenzyme Q10, ascorbic acid, retinol and retinyl derivatives, bisabolol, allantoin, phytantriol, panthenol, AHA acids, amino acids, ceramides, essential oils, hyaloronic acid, creatine, protein hydrolysates, plant extracts, peptides and vitamin complexes.

In a further preferred embodiment, a microemulsion is used comprising (all data based on active substance (AS)):
  4-25% by weight of component (a)
  4-20% by weight of component (b)
  5-50% by weight of component (c)
  0.5-15% by weight of component (d)
  ad 100% by weight of component (e)
  0-10% by weight of component (f)
  0-5% by weight of other ingredients (g),
with the proviso that the sum of (a) to (g) gives 100.

The microemulsions can be formulated free from the cationic component (f). The following compositions are then preferred for the use for producing hand dishwashing detergents (based on AS):
  4-25% by weight of component (a) alkyl(oligo)glycoside
  4-20% by weight of component (b) cosurfactant—preferably a glycerol ester
  5-50% by weight of component (c) organic oil phase—preferably a dialkyl ether
  0.5-15% by weight of component (d) wax—preferably an alkyl ester and
  0-5% by weight of further ingredients (g),
and the remainder to 100% by weight is water.

Also advantageous are microemulsions which comprise cationic components (f) (all data based on AS). Here, the following quantitative ranges are preferred for producing hand dishwashing detergents:
  4-25% by weight of component (a) alkyl(oligo)glycoside
  4-20% by weight of component (b) cosurfactant—preferably a glycerol ester
  5-50% by weight of component (c) organic oil phase—preferably a dialkyl ether
  0.5-15% by weight of component (d) wax—preferably an alkyl ester
  0.5-10% by weight of component (f) and
  0-5% by weight of other ingredients (g),
and the remainder to 100% by weight of water.

The aqueous microemulsions according to the present description preferably have a pH between 2 and 9, where the ranges from 3 to 8 can be advantageous.

Production of the Microemulsions

These emulsions are produced for example by firstly, in a first step, preparing a microemulsion comprising preferably at least 10-20% by weight of an alkyl (oligo)glycoside of the general formula $R^1O-[G]_p$, in which $R^1$ is an alkyl and/or alkenyl radical having 4 to 22 carbon atoms, G is a sugar radical having 5 or 6 carbon atoms and p is numbers from 1 to 10, and adding preferably 1-30% by weight of a cosurfactant and preferably 5-50% by weight of an oil body and the remainder to 100% by weight of water, and stirring this mixture, optionally with heating to temperatures of 30 to 80° C.

In a preferred embodiment, the microemulsions are produced according to the teaching of WO 08/155,075 A1, the process disclosed therein is a two-stage process in which, in the first step, a microemulsion is produced in a manner known per se. The microemulsions in step 1 are preferably produced by mixing the oil phase with the further oil-soluble ingredients, heating the oil phase to above the melting point of all of the constituents and then adding the aqueous surfactant-containing phase. The thermodynamically stable microemulsion is then formed spontaneously, if necessary with additional stirring.

According to the invention, the microemulsions are added to cleaning agents known per se in order to improve the skin friendliness of these. Preferably, the microemulsions are added to hand dishwashing detergents and cosmetic cleaning agents, in particular shower gels. For this, it is advantageous if the microemulsion is mixed with the other constituents of the cleaning agent at temperatures of from 35 to 65° C., preferably from 40 to 50° C. On account of the fraction of the water-insoluble oil phase, and/or the wax component, lower processing temperatures may result in clouding of the emulsion.

Depending on the requirement profile, the microemulsion is used directly.

Within the context of the invention, the microemulsion can be used with further additives as cosmetic cleaning agent.

Accordingly, the invention further logically provides a cosmetic cleaning agent which comprises A) the microemulsion according to the invention. Furthermore, the cosmetic cleaning agent according to the invention comprises
  B) anionic surfactants, preferably alkoxylated, such as, for example sodium lauryl ether sulfate,
  C) cationic polymers,
  D) optionally further surfactants,
  E) optionally further cosmetic additives and
  F) water.

As well as cosmetic cleaning agents, the microemulsions are preferably added to liquid non-cosmetic cleaning agents since this is advantageous both from the point of view of processing and also effect. The non-cosmetic cleaning agents typically comprise anionic and/or amphoteric and/or nonionic surfactants as well as water and optionally further ingredients typical for such agents.

Within the context of the present technical teaching, non-cosmetic cleaning agents are understood in particular as meaning those agents which, upon use, can come into direct contact with the human skin. These include in particular all-purpose cleaners, bath or kitchen cleaners, floor and carpet cleaners and hand dishwashing detergents.

The cosmetic cleaning agents produced according to the invention in the form of finely divided emulsions can be used for producing cosmetic cleaning agents, such as, for example, shower gels, shower baths, hair shampoos, hair lotions, foam baths, hand washing products, face cleaners, make-up removers, bath preparations, baby care products, creams, gels, lotions, alcoholic and aqueous/alcoholic solutions, emulsions, wax/fat masses, stick preparations, powders or ointments.

Preference is given to low viscosity, transparent to slightly cloudy gels for cleaning skin or hair. The microemulsions and also the cosmetic cleaning agents can serve as impregnation medium for wipes, fabric, which are used wet or dry by the user or else are applied from a pump foamer.

Both the cosmetic and the non-cosmetic cleaning agents are produced in a manner known per se. The microemulsions according to the above description are added to the ingredients of the cleaning agents, the effect according to the invention only occurring when the finished microemulsion with all of the ingredients as intended is brought together with the remaining ingredients of the cleaning agent.

The addition of individual constituents does not lead to the desired result; what is essential here is the feature of the microemulsion for realizing the present teaching.

For producing clear products, it is also preferred that the addition of the microemulsion to the further constituents of the cleaning agent is undertaken at slightly elevated temperatures, preferably at 30 to 60° C., in order to achieve complete mixing.

In a preferred embodiment, the cosmetic cleaning agent according to the invention comprises
- A 0.1 to 20% by weight of a microemulsion to be used according to the invention
- B 5-20% by weight of anionic surfactants
- C 0.02-2% by weight of cationic polymers
- D 0-15% by weight of further surfactants
- E 0-10% by weight of cosmetic additives
- F water ad 100%.

In a further preferred embodiment, the cosmetic cleaning agent according to the invention consists of
- A 0.1 to 20% by weight of a microemulsion to be used according to the invention
- B 5-20% by weight of anionic surfactants
- C 0.02-2% by weight of cationic polymers
- D 0-15% by weight of further surfactants
- E 0-10% by weight of cosmetic additives
- F water ad 100%.

Particular preference is given to a cosmetic cleaning agent comprising
- A 0.2-10% by weight of a microemulsion to be used according to the invention
- B 8-15% by weight of anionic surfactants
- C 0.05-1% by weight of cationic polymers
- D 0-5% by weight of further surfactants
- E 0-10% by weight of cosmetic additives
- F water ad 100%.

As described above, as well as the microemulsion according to the invention, the cosmetic cleaning agents according to the invention also comprise further components such as B) the anionic surfactants which are selected from the group which is formed from soaps, alkylbenzenesulfonates, alkanesulfonates, olefinsulfonates, alkyl ether sulfonates, glycerol ether sulfonates, α-methyl ester sulfonates, sulfo fatty acids, alkyl sulfates, fatty alcohol ether sulfates, glycerol ether sulfates, fatty acid ether sulfates, hydroxyl mixed ether sulfates, monoglyceride(ether)sulfates, fatty acid amide(ether)sulfates, mono- and dialkyl sulfosuccinates, mono- and dialkyl sulfosuccinamates, sulfotriglycerides, amide soaps, ether carboxylic acids and salts thereof, fatty acid isethianates, fatty acid arcosinates, fatty acid taurides, N-acylamino acids, such as, for example, acyl lactylates, acyl tartrates, acyl glutamates and acyl aspartates, alkyl oligoglucoside sulfates, protein fatty acid condensates (in particular wheat-based vegetable products) and alkyl(ether)phosphates; particular preference is given here to the fatty alcohol ether sulfates, such as, for example, sodium lauryl ether sulfates or other compounds with comparable foaming behavior for use as cleaning care agents such as shower gel, shampoo, hand washing agents or the like.

Cationic Polymers C)

As component C), the cosmetic agents of the present patent application comprise the cationic polymers described above.

Further Surfactants D)

As components D), the cosmetic agents of the present patent application comprise further surfactants. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partially oxidized alk(en)yl oligoglycosides or glucoronic acid derivatives, fatty acid N alkylglucamides, protein hydrolysates (in particular wheat-based vegetable products), polyol fatty acid esters, sugar esters, sorbitan esters, polysorbates and amine oxides. If the nonionic surfactants contain polyglycol ether chains, these can have a conventional homolog distribution, but preferably have a narrowed homolog distribution. Typical examples of cationic surfactants are quaternary ammonium compounds, such as, for example, dimethydistearylammonium chloride, and ester quats, in particular quaternized fatty acid trialkanolamine ester salts.

Within the context of the invention, preferred further surfactants are amphoteric or zwitterionic surfactants. Typical examples of amphoteric or zwitterionic surfactants are alkyl betaines, alkylamido betaines, aminopropionates, aminoglycinates, imidazolinium betaines and sulfobetaines, particular preference being given to cocamidopropyl betaine. The specified surfactants are exclusively known compounds. Typical examples of particularly suitable mild, i.e. particularly skin-compatible, surfactants are fatty alcohol polyglycol ether sulfates, monoglyceride sulfates, mono- and/or dialkyl sulfosuccinates, fatty acid isothionates, fatty acid arcosinates, fatty acid taurides, fatty acid glutamates, α-olefinsulfonates, ether carboxylic acids, alkyl oligoglucosides, fatty acid glucamides, alkylamido betaines such as cocamidopropyl betaine, amphoacetates such as sodium cocoamphoacetate and/or protein fatty acid condensates, the latter preferably based on wheat proteins.

Cosmetic Additives E)

The further components E) of the cosmetic additives has already been described above. Within the context of the invention, it is preferred that the described cosmetic additives are present in the cosmetic cleaning agent and are not incorporated into the microemulsion. However, if the microemulsion is used without further components (B to E), it can comprise these additives. For the use as cleaning gel or as paste and ointment, consistency regulators and thickeners are preferably present as cosmetic additives. These can be selected from the following compounds:

Consistency Regulator and Thickener

Suitable consistency regulators are primarily fatty alcohols or hydroxy fatty alcohols having 12 to 22 and preferably 16 to 18 carbon atoms and in addition partial glycerides, fatty acids or hydroxy fatty acids. Preference is given to a combination of these substances with alkyl oligoglucosides and/or fatty acid N-methyl glucamides of identical chain length and/or polyglycerol poly-12-hydroxystearates. Suitable thickeners are, for example, Aerosil grades (hydrophilic silicas), polysaccharides, in particular xanthan gum, guar guar, agar agar, alginates and tyloses, carboxymethyl cellulose and hydroxyethyl cellulose and hydroxypropyl cellulose, in addition high molecular weight polyethylene glycol mono- and diesters of fatty acids, polyacrylates and hydrophobically modified polyacrylates, polyacrylamides, polymers, polyvinyl alcohol and polyvinyl pyrrolidone. Bentonites, which are a mixture of cyclopentasiloxane, disteardimonium hectorite and propylene carbonate, have also proven to be particularly effective. Also of suitability are surfactants such as, for example, ethoxylated fatty acid glycerides, esters of fatty acids with polyols such as, for example, pentaerythritol or trimethylolpropane, fatty alcohol ethoxylates with a narrowed homolog distribution or alkyl oligoglucosides, and also electrolytes such as sodium chloride and ammonium chloride.

If preservatives are used according to the invention, these are preferably selected from the group which is formed from benzoic acid and salts thereof, citric acid and salts thereof, phenoxyethanol, benzyl alcohol, alkylparabens, preferably ethyl-, methyl- and propylparaben. Suitable preservatives are also, for example, formaldehyde solution, pentanediol, or sorbic acid, and also the silver complexes known under the name Surfacine® and the other substance classes listed in Annex 6, Part A and B of the Cosmetics Ordinance.

By incorporating a microemulsion as component A) into the cosmetic cleaning agents according to the invention, the transparent to slightly cloudy incorporation of relatively large amounts of oil bodies is possible, said oil bodies then, with the cationic polymers of component C) in the composition stabilized by the surfactants of component B), bringing about the excellent conditioning properties of the preparation.

For producing non-cosmetic cleaning agents, preferably hand dishwashing detergents, the addition of the ingredients typical for these cleaning agents, such as surfactants, is preferred according to the invention.

Typical examples of anionic surfactants are also here the surfactants listed for cosmetic cleaning agents as component B). If the anionic surfactants contain polyglycol ether chains, these can have a conventional homolog distribution, but preferably have a narrowed homolog distribution.

Typical examples of nonionic surfactants, cationic and amphoteric and/or zwitterionic surfactants correspond to the selection described as component D) for cosmetic cleaning agents.

For producing non-cosmetic cleaning agents, anionic surfactants are particularly preferably present, and here in particular alkyl ether sulfates.

Alkyl ether sulfates ("ether sulfates") are known anionic surfactants which are produced on an industrial scale by $SO_3$— or chlorosulfonic acid (CSA) sulfation of fatty alcohol or oxo alcohol polyglycol ethers and subsequent neutralization. Within the context of the invention, suitable ether sulfates are those which conform to the formula (II), $R^2O-(CH_2CH_2O)_mSO_3X$ (II), in which $R^2$ is a linear or branched alkyl and/or alkenyl radical having 6 to 22 carbon atoms, n is numbers from 1 to 10 and X is an alkali metal and/or alkaline earth metal, ammonium, alkylammonium, alkanolammonium or glucammonium. Typical examples are the sulfates of addition products of, on average, 1 to 10 and in particular 2 to 5 mol of ethylene oxide onto caproic alcohol, caprylic alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and brassidyl alcohol, and technical-grade mixtures thereof in the form of their sodium and/or magnesium salts. The ether sulfates here can have either a conventional homolog distribution or a narrowed homolog distribution. Particular preference is given to using ether sulfates based on adducts of, on average, 2 to 3 mol of ethylene oxide onto technical-grade $C_{12/14}$ or $C_{12/18}$ coconut fatty alcohol fractions in the form of their sodium and/or magnesium salts.

The non-cosmetic cleaning agents can also comprise dyes, fragrances, pearlizing agents, opacifiers, complexing agents inorganic or organic acids and/or bases, builders, bleaches, antifoams, but also polymers (e.g. as thickeners but also as builders), hydrotopes and solubility promoters and the like. Preferably, the non-cosmetic cleaning agents comprise polymers, reference being made in this respect as regards the details to the above description. These substances are then usually used in amounts of in total up to 20% by weight, but preferably only up to at most 15% by weight and in particular from 1.5 to 5% by weight, based on the total weight of the non-cosmetic cleaning agents.

The pH of the cleaning agents is preferably in the range from 4.0 to 10.0, preferably 5.5 to 8.0. Preferably, the non-cosmetic cleaning agents have a pH in the range from 6 to 7.5. In the case of acidic cleaners, as are often used in the bath sector, however, considerably lower pH values, typically from 2 to 5, preferably from 3.5 to 4.5, are also possible. For cosmetic cleaning agents, a pH range 4-8 is preferred.

The application further provides the use of microemulsions according to the above description for improving the sensory properties of cleaning agents, in particular of aqueous hand dishwashing detergents and/or of cosmetic cleaning agents such as shower gel and hair shampoo.

Sensory properties are understood as meaning the properties of agents which can lead to a change in the sensory perception by people, thus in the present case is meant in particular the skin feel which is triggered by direct contact of the human skin with one substance or a substance mixture. In practice, this skin feel is ascertained e.g. by a panel test on subjects who qualify their sensory impressions in relation to certain parameters, such as "dryness of the skin", "softness of the skin" etc. by means of gradings.

By adding the microemulsions according to the invention to cleaning agents, it is possible to improve these sensory impressions of the subjects following contact with the particular cleaning agent.

The microemulsions are used preferably in amounts of from 0.1 to 20% by weight, preferably from 0.2 to 10% by weight, based on the total weight of the cleaning agent, in order to achieve the desired success.

A last subject matter therefore relates to an aqueous hand dishwashing detergent comprising anionic and amphoteric surfactants, and also, in amounts of from 0.2 to 10% by weight, based on the total weight of the hand dishwashing detergent, a microemulsion according to the above description. Such hand dishwashing detergents can also further comprise 5 to 25% by weight of anionic surfactants, 5 to 25% by weight of amphoteric surfactants and 0 to 1% by weight of cationic polymers (preferably of the PQ-7 type and/or PQ-10 type [according to INCI]), and also water up to 100% by weight.

EXAMPLES

1. Formulations for Hand Dishwashing Detergents

The following microemulsions M1 and M2 were produced for use in hand dishwashing detergents:

TABLE 1

Microemulsions for hand dishwashing detergents

| Ingredients | M1 Amount [% by wt.] | M2 Amount [% by wt.] |
| --- | --- | --- |
| Glycerol monooleate | 8.0 | 8.0 |
| Dioctyl ether | 25.0 | 25.0 |
| Hexadecyl hexadecanoate | 10.0 | 10.0 |

TABLE 1-continued

Microemulsions for hand dishwashing detergents

| Ingredients | M1 Amount [% by wt.] | M2 Amount [% by wt.] |
|---|---|---|
| $C_{12}$-$C_{16}$ fatty alcohol 1,4-glucoside (50% AS) | 20.4 | 20.4 |
| $C_8$-$C_{16}$ fatty alcohol 1,4-glucoside (50% AS) | 13.6 | 13.6 |
| Trimethylhexadecylammonium chloride | — | 5.0 |
| Benzoic acid | 1.0 | 1.0 |
| Citric acid | 2.0 | 2.0 |
| Transmission at 40° C. | 99% | 99% |
| Water | Remainder to 100% by weight | Remainder to 100% by weight |

The two microemulsions M1 and M2 were used to produce two hand dishwashing detergents H1 and H2
for comparison, an agent H3 without microemulsion was used—all quantitative data in the table refer to active substance (AS):

TABLE 2

Formulations for hand dishwashing detergents

| Ingredients | H1 Amount [% by wt.] | H2 Amount [% by wt.] | H3 Amount [% by wt.] |
|---|---|---|---|
| Alkyl ether sulfate [1] | 12.0 | 12.0 | 12.0 |
| Dimethylcocoacylamidopropyl-ammonium acetobetaine [2] | 3.0 | 3.0 | 3.0 |
| Cationic polymer | 0.50 | — | — |
| Microemulsion M1 | 5.0 | — | — |
| Microemulsion M2 | — | 10.0 | — |
| Thickener [3] | 1.56 | 1.56 | — |
| Biocide [4] | 0.2 | 0.2 | 0.2 |
| NaCl | 1.0 | 1.0 | — |
| Water | Remainder to 100% by weight | Remainder to 100% by weight | Remainder to 100% by weight |

[1] Texapon N 70 (Cognis)
[2] Dehyton K (Cognis)
[3] Arlypon TT (Cognis)
[4] Microcare IT (Thor)

The three formulations H1-H3 were tested in pairs in a forearm test by test subjects. For this purpose, the agents were dripped onto the wetted forearm of the test subjects in a concentration of 10 g/l and left there for 30 seconds. The arm was then rinsed with water for 5 seconds. The test subjects were asked to assess their impressions for the areas "spreading of the agent", "softness following application", "softness after 30 seconds", "smoothness after application and after 30 seconds", "dryness after application and after 30 seconds" and "acceptance". Formulations H1 and H3, and also formulations H2 and H3 were tested against one another.

Here, it was found that in each case formulation H1 was preferred over H3, and formulation H2 was preferred over H3.

2. Formulations for Shower Gels

The formulations below are intended to illustrate the present invention without limiting it. Unless stated otherwise, all quantitative data, fractions and percentages are percentages by weight (% by wt.), based on the weight and the total amount or on the total weight of the preparations. The percentages by weight given in the examples are active contents or percentage by weight of active substance.

All of the substances are products from Cognis. All substance names are registered trademarks.

The microemulsion according to the invention for cosmetic cleaning agents—example formulation M3 to M7

TABLE 3

Microemulsion for cosmetic cleaning agents, conductivity 0.25 mSi/cm, viscosities 5000-20 000 mPa s, pH = 3.2-4.5

| | | | Active substance % by wt. | | | | |
|---|---|---|---|---|---|---|---|
| | Substance | INCI | M3 | M4 | M5 | M6 | M7 |
| 1 | Cetiol 88 | Caprylyl caprylate | 38.5 | 39.0 | 42.5 | 33 | 36 |
| 2 | Plantacare 1200 UP | Lauryl glycoside | 20 | 19.0 | 17.5 | 17.5 | 19 |
| 3 | Dehymuls PGPH | Polyglyceryl-2 dipolyhydroxy-stearate | 8.5 | 8.5 | 7.5 | 7.5 | 8 |
| 4 | Lameform TGI | Polyglyceryl-3 diisostearate | 8.5 | 8.5 | 7.5 | 7.5 | 8 |
| 5 | Cegesoft SB | Shea butter | 3.8 | 3.0 | 3.0 | 3.0 | 2.5 |
| | Citric Acid | | q.s. | q.s. | q.s. | q.s. | q.s. |
| 6 | Water | | ad 100 | ad 100 | ad 100 | ad 100 | ad 100 |

The microemulsions were produced by mixing the components with stirring at a temperature of 75° C. The viscosity was determined using a Brookfield viscometer, spindle 2, at 20 rpm.

To produce the shower gels, one of the aforementioned microemulsion M3 to M7 (M4) was mixed into the following formulation in a further step. A transparent emulsion is formed.

TABLE 4

Shower gel formulations, B and C comprise the microemulsion, A, D and E serve as comparison formulation.

| | Substance | INCI | A | B | C | D | E |
|---|---|---|---|---|---|---|---|
| 1 | Texapon N70 | Sodium laureth sulfate + 2EO | 9 | 9 | 9 | | 10 |
| 2 | Dehyton PK45 | Cocamido-propylbetaine | 3 | 3 | | 2.1 | 2 |
| 3 | Plantacare 2000UP | | | | | 7.7 | |
| | Sulfopon 1216G | | | | | 5.2 | |
| 3 | Microemulsion M4 (as in Table 3) | | 0 | 2.0 | 4.0 | | |
| 4 | JR-400 | PQ-10 | | | | 0.2 | |
| 5 | Jaguar C162 | Hydroxypropyl guar, hydroxypropyl-trimonium chloride | 0.2 | 0.2 | 0.2 | | |
| | Guar TC | | | | | | 0.2 |
| 6 | Arlypon TT | PEG-120-PPG-10-trimethylol-propane trioleate | 0.6 | 0.8 | 1.0 | | 1 |
| | Rheocare XG | Xanthan | | | | 1.0 | |
| 7 | Dekafeld | DMDM Hydantoin | 0.2 | 0.2 | 0.2 | | 0.2 |
| | Sodium benzoate | | | | | 1.0 | |
| 8 | NaCl | | 1.0 | 1.0 | 1.0 | | 1.0 |

TABLE 4-continued

Shower gel formulations, B and C comprise the microemulsion, A, D and E serve as comparison formulation.

| | Substance | INCI | A | B | C | D | E |
|---|---|---|---|---|---|---|---|
| 9 | Water | | ad 100 | ad 100 | ad 100 | ad 100 | ad 100 |

Deposition of Lipid Components on the Skin—Detection of Cetiol 88

Formulations F to I were investigated by test subjects as to their property of deposition of lipid components. The aim was to determine how the concentration on the skin of defined lipids after using the formulations according to the invention behaves compared to formulations without the microemulsion M3 to M7 described in the invention comprising ester oils and waxes, specifically shea butter. For this, the arms of the test subjects were prewashed with 13% strength Texapon NSO solution, a blank value was determined and the areas to be treated were divided up. 1 g of product was rubbed into the respective area by the test leader for 45 s and then the area was rinsed with 950 ml of water in a defined manner. A glass cylinder was placed on flush, filled with 3 ml of ethanol and rubbed onto the skin for 1 min. using a glass rod. The eluates were transferred to vials by means of Pasteur pipette and analyzed by means of GC/MS coupling. The concentrations were given in $\mu g/cm^2$.

| | Substance | INCI | F | G | H | I |
|---|---|---|---|---|---|---|
| 1 | Texapon N70 | Sodium laureth sulfate + 2EO | 9 | 9 | 9 | 9 |
| 2 | Dehyton PK45 | Cocamidopropylbetaine | 3 | 3 | 3 | 3 |
| 3 | Microemulsion M4 (as in Table 3) | | 0 | 1.0 | 4.1 | 10.0 |
| 4 | Jaguar C162 | Hydroxypropyl guar, hydroxypropyltrimonium chloride | 0.2 | 0.2 | 0.2 | 0.2 |
| 5 | Arlypon TT | PEG-120-PPG-10-trimethylolpropane trioleate | 0.9 | 1.0 | 1.0 | 1.7 |
| 6 | Dekafeld | DMDM Hydantoin | 0.2 | 0.2 | 0.2 | 0.2 |
| 7 | NaCl | | 1.0 | 1.0 | 1.0 | 1.0 |
| 8 | Water | | ad 100 | ad 100 | ad 100 | ad 100 |
| | Deposition of Cetiol 88 [$\mu g/cm^2$] | | 0.09 | 0.41 | 1.00 | 3.73 |

The results in the last line of the table clearly show that by using the wax-containing microemulsion, a significantly higher deposition of the lipid component is recorded. These tests show which positive effects the wax-containing microemulsion has on the skin. The negative effects of the washing-active substances, such as, for example, destruction of the lipid film on the skin and drying out of the skin, is cancelled out by using the wax-containing microemulsion without, however, reducing or destroying the positive cleaning effects of the washing-active substances.

The invention claimed is:

1. A method for producing a cleaning agent, the method comprising adding a microemulsion comprising:
    (a) at least one alkyl (oligo)glycoside;
    (b) at least one cosurfactant different from (a) comprising a polyglyceryl fatty acid ester;
    (c) at least one non-water-soluble organic oil;
    (d) at least one wax that is a solid at 21° C.; and
    (e) water
    to a cleaning agent component to form the cleaning agent.

2. The method of claim 1, wherein the microemulsion comprises an alkyl(oligo)glycoside (a) according to the general formula $R^1O\text{-}[G]_p$, in which $R^1$ is an alkyl and/or alkenyl radical having 4 to 22 carbon atoms, G is a sugar radical having 5 or 6 carbon atoms and p is numbers from 1 to 10.

3. The method of claim 1, wherein the non-water-soluble organic oil component (c) is selected from the group consisting of branched fatty alcohols, $C_6\text{-}C_{22}$ dialkyl ethers, ester oils, hydrocarbons, and mixtures thereof.

4. The method of claim 1, wherein the cleaning agent comprises a shower gel or a shampoo, wherein the non-water-soluble organic oil component (c) is selected from the group consisting of esters of linear $C_6\text{-}C_{22}$ fatty acids with linear or branched $C_6\text{-}C_{22}$ fatty alcohols, esters of branched $C_6\text{-}C_{13}$ carboxylic acids with linear or branched $C_6\text{-}C_{22}$ fatty alcohols, esters of linear $C_6\text{-}C_{22}$ fatty acids with branched alcohols, esters of $C_{18}\text{-}C_{38}$ alkylhydroxylcarboxylic acids with linear or branched $C_6\text{-}C_{22}$ fatty alcohols, esters of linear and/or branched fatty acids with polyhydric alcohols and/or Guerbet alcohols, esters of $C_6\text{-}C_{22}$ fatty alcohols and/or Guerbet alcohols with aromatic carboxylic acids, esters of $C_2\text{-}C_{12}$ dicarboxylic acids with linear or branched alcohols having 1 to 22 carbon atoms or polyols having 2 to 10 carbon atoms and 2 to 6 hydroxyl groups, linear and branched $C_6\text{-}C_{22}$ fatty alcohol carbonates, isopropyl palmitate, isopropyl myristate, ethylhexyl palmitate, cetyl palmitate, myristyl myristate, oleyl oleate, ethylhexyl stearates, di-n-octyl carbonates, caprylyl caprylate, oleyl erucate, and mixtures thereof.

5. The method of claim 1, wherein the wax component (d) comprises a natural wax; a chemically modified wax or a synthetic wax.

6. The method of claim 1, wherein the microemulsion further comprises a cationic compound as additional component (f).

7. The method of claim 1, wherein the microemulsion further comprises as component (g) an ingredient that is selected from the group consisting of glycerol, preservatives, citric acid, phenoxyethanol, UV photoprotective filters, antioxidants, biogenic active ingredients, perfume, dyes, biocides, and pH regulators.

8. The method of claim 1, wherein the microemulsion comprises:
    4-25% by weight of component (a);
    4-20% by weight of component (b);
    5-50% by weight of component (c);
    0.5-15% by weight of component (d);
    0-10% by weight of a cationic compound, component (f);
    0-5% by weight of a further ingredient (g), and
    component (e) in an amount such that the sum of (a) to (g) gives 100.

9. The method of claim 1, the sensory properties of the cleaning agent is improved.

10. An aqueous hand dishwashing detergent comprising anionic and amphoteric surfactants, and, in amounts of 0.2 to 10% by weight, based on the total weight of the hand dishwashing detergent, a microemulsion according to claim 1.

11. A cosmetic cleaning agent comprising:
    a microemulsion according to claim 1;
    an anionic surfactant;
    a cationic polymer;
    optionally, a further surfactant;
    optionally, one or more cosmetic additives; and
    water.

12. The method of claim 9, wherein the cleaning agent is in wipes, shower gels, shower baths, hair shampoos, hair lotions, foam baths, hand washing agents, face cleaners, make-up removers, bath preparations, baby care products, creams, gels, lotions, alcoholic and aqueous/alcoholic solutions, emulsions, wax/fat masses, stick preparations, powders, or ointments.

13. The method of claim 5, wherein the wax component (d) comprises the natural wax comprising shorea stenoptera butter, shea butter, candelilla wax, carnauba wax, Japan wax, esparto grass wax, cork wax, guaruma wax, rice germ oil wax, sugar cane wax, ouricury wax, montan wax, beeswax, shellac wax, spermaceti, lanolin (wool wax), uropygial grease, ceresine, ozokerite (earth wax), petrolatum, paraffin wax, or micro wax.

14. The method of claim 5, wherein the wax component (d) comprises the chemically modified wax comprising a montan ester wax, a sasol wax, or a hydrogenated jojoba wax.

15. The method of claim 5, wherein the wax component (d) comprises the synthetic wax comprising a polyalkylene wax, a polyethylene glycol waxes, a wax based on an ester of a monocarboxylic acid having at least 14 carbon atoms with a fatty alcohol having at least 14 carbon atoms.

16. The method of claim 6, wherein the cationic compound comprises a quaternary ammonium compound and/or a cationic polymer.

17. The method of claim 1, wherein the non-water-soluble organic oil component (c) comprises an ester oil comprising an ester of branched or linear monocarboxylic acids having 6 to 22 carbon atoms with linear or branched fatty alcohols having 6 to 22 carbon atoms.

\* \* \* \* \*